United States Patent
Pisarenco et al.

(10) Patent No.: US 10,408,753 B2
(45) Date of Patent: Sep. 10, 2019

(54) METHOD AND APPARATUS FOR CALCULATING ELECTROMAGNETIC SCATTERING PROPERTIES OF FINITE PERIODIC STRUCTURES

(75) Inventors: Maxim Pisarenco, Eindhoven (NL); Irwan Dani Setija, Utrecht (NL)

(73) Assignee: ASML Netherlands B.V., Veldhoven (NL)

( * ) Notice: Subject to any disclaimer, the term of this patent is extended or adjusted under 35 U.S.C. 154(b) by 2007 days.

(21) Appl. No.: 13/490,416

(22) Filed: Jun. 6, 2012

(65) Prior Publication Data
US 2013/0144560 A1  Jun. 6, 2013

Related U.S. Application Data

(60) Provisional application No. 61/504,908, filed on Jul. 6, 2011.

(51) Int. Cl.
| | | |
|---|---|---|
| *G01N 21/47* | (2006.01) | |
| *G06F 17/00* | (2019.01) | |
| *G03F 7/20* | (2006.01) | |

(52) U.S. Cl.
CPC ............ *G01N 21/47* (2013.01); *G03F 7/705* (2013.01); *G03F 7/70625* (2013.01); *G03F 7/70633* (2013.01); *G06F 17/00* (2013.01); *G01N 21/4788* (2013.01)

(58) Field of Classification Search
CPC ......... G01N 21/47; G06F 17/00; G03F 7/705; G03F 7/70625; G03F 7/70633; G03F 17/00
USPC ........................................................ 702/189
See application file for complete search history.

(56) References Cited

U.S. PATENT DOCUMENTS

| | | | |
|---|---|---|---|
| 7,652,765 B1* | 1/2010 | Geshwind et al. | 356/330 |
| 2006/0066855 A1* | 3/2006 | Boef et al. | 356/401 |
| 2011/0098992 A1* | 4/2011 | Van Beurden | G03F 7/705 |
| | | | 703/2 |

OTHER PUBLICATIONS

Scattering Theory and Linear Least Squares Estimation: Part II—Discrete Time Problems, 1975.*
Hugonin, J.P., and Lalanne, P., "Perfectly matched layers as nonlinear coordinate transforms: a generalized formalization," *J. Opt. Soc. Am.* vol. 22 No. 9:1844-1849, Optical Society of America (Sep. 2005).
Pisarenco, M., et al., "Aperiodic Fourier modal method in contrast-field formulation for simulation of scattering from finite strictures," *J. Opt. Soc. Am.* vol. 27 No. 11:2423-2431, Optical Society of America (Nov. 2010).
Redheffer, R., "Difference Equations and Functional Equations in Transmission-line Theory," *Modern Mathematics for the Engineer* (E.F. Beckenbach ed., McGraw-Hill Book Company, Inc. 1961); pp. 282-337.

* cited by examiner

*Primary Examiner* — Sujoy K Kundu
*Assistant Examiner* — Lynda Dinh
(74) *Attorney, Agent, or Firm* — Sterne, Kessler, Goldstein & Fox P.L.L.C.

(57) ABSTRACT

A method for calculating electromagnetic scattering properties of a finite periodic structure having a direction of periodicity is disclosed. The method numerically calculates electromagnetic scattering properties using spatial discretization in the direction of periodicity and numerically calculates electromagnetic scattering properties using spectral discretization in a direction orthogonal to the direction of periodicity.

17 Claims, 9 Drawing Sheets

METHOD AND APPARATUS FOR CALCULATING ELECTROMAGNETIC SCATTERING PROPERTIES OF FINITE PERIODIC STRUCTURES

CROSS REFERENCE TO RELATED APPLICATIONS

This application claims the benefit wider 35 U.S.C. § 119(e) to U.S. Provisional Patent Application No. 61/504,908, filed Jul. 6, 2011, which is incorporated by reference herein in its entirety.

FIELD

The present invention relates to methods and inspection apparatus for calculating electromagnetic scattering properties of finite periodic structures and reconstructing an approximate structure of such finite periodic structures. The present invention is usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly-resolved scatterometers use a monochromatic radiation beam and measure the intensity of the scattered radiation as a function of angle.

SUMMARY

According to a first aspect of the present invention, there is provided a method of calculating electromagnetic scattering properties of a finite periodic structure having a direction of periodicity, the method comprising numerically calculating electromagnetic scattering properties using spatial discretization in the direction of periodicity and spectral discretization in a direction orthogonal to the direction of periodicity.

According to an aspect of the present invention, there is provided a method of reconstructing an approximate structure of a finite periodic structure from a detected electromagnetic scattering property arising from illumination of the finite periodic structure by radiation, the method comprising estimating at least one structural parameter, determining at least one model electromagnetic scattering property from the at least one structural parameter, comparing the detected electromagnetic scattering property to the at least one model electromagnetic scattering property, and determining an approximate structure of the finite periodic structure based on the result of the comparison.

According to an aspect of the present invention, there is provided an inspection apparatus for reconstructing an approximate structure of a finite periodic structure, the inspection apparatus comprising an illumination system configured to illuminate the finite periodic structure with radiation, a detection system configured to detect an electromagnetic scattering property arising from the illumination. A processor configured to estimate at least one structural parameter, determine at least one model electromagnetic scattering property from the at least one structural parameter, compare the detected electromagnetic scattering property to the at least one model electromagnetic scattering property, and determine an approximate structure of the finite periodic structure from a difference between the detected electromagnetic scattering property and the at least one model electromagnetic scattering property.

According to an aspect of the present invention, there is provided a computer program product containing one or more sequences of machine-readable instructions for calculating electromagnetic scattering properties of a structure, the instructions being adapted to cause one or more processors to perform a method according to the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 7:
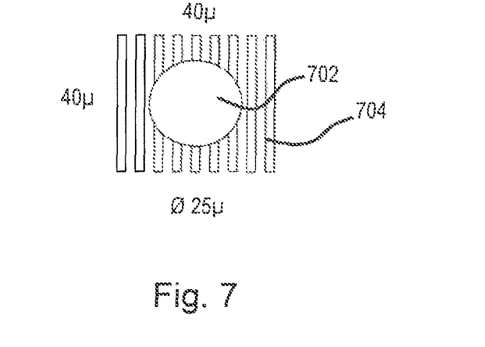
FIG. 7 illustrates a scatterometer spot size smaller than the target grating, an "underfill".

The angularly-resolved scatterometric principle is based on profile reconstruction from an angularly-resolved scattering spectrum. With reference to FIG. 7, a focused incoherent beam 702 is scattered from a target grating 704 that is larger than the illumination spot 702. This is called "underfill". The target profile is then reconstructed by comparing the measured spectrum to a computed spectrum from a parameterized profile. In the typical implementation of spectrum calculation, the complex reflection coefficients from the grating are computed using a rigorous diffraction model with periodic boundary conditions, for example Rigorous Coupled-Wave Analysis (RCWA). This has a computational advantage: due to the periodicity, the solution to Maxwell's equations only needs to be found in one period. This allows all fields and refractive index variations to be efficiently discretized by way of Fourier series. The fact that the illumination profile is not periodic, can be overcome by describing the focused beam as an infinite sum of incoherent plane waves. For each plane wave, the diffraction problem is solved and the reflected waves are incoherently added.

An important condition for the application of periodic boundary conditions is that the light does not "see" the edges of the grating. For a 25 μM diameter spot on a 40×40 μm² grating, this condition is well fulfilled.

Typical CD-reconstruction and overlay measurement in angularly resolved scatterometers takes place on such 40×40 μm² metrology targets placed in the scribe lane. The trend in Wafer Metrology, however, is towards measurement of CD and overlay (OV) on small in-die targets ~10×10 μm² and it is expected that CD reconstruction in the near future will also take place on such small gratings. For incoherent illumination it is difficult to reduce the spot to a size much smaller than 10 μm. For these sizes, the infinitely periodic grating assumption is invalid and the finite size of the grating must be taken into account. This leads to the illumination spot partly overlapping the metrology target boundaries. For CD reconstruction, this will lead to edge diffraction effects. The current rigorous diffraction models for 2-D and 3-D structures assume infinite periodicity in one or two directions respectively which is only valid if the illumination spot is much smaller than the metrology grating. When the light "sees" the edges, the finite size must be appropriately included in the modeling.

Finite-difference time-domain (FDTD) and Finite element method (FEM) are rigorous diffraction models that can cope with the non-periodicity without solving the problem on an infinite domain. They do this by placing a Perfectly Matched Layer (PML) around the object. This PML acts as a perfectly absorbing layer.

Figure 8:
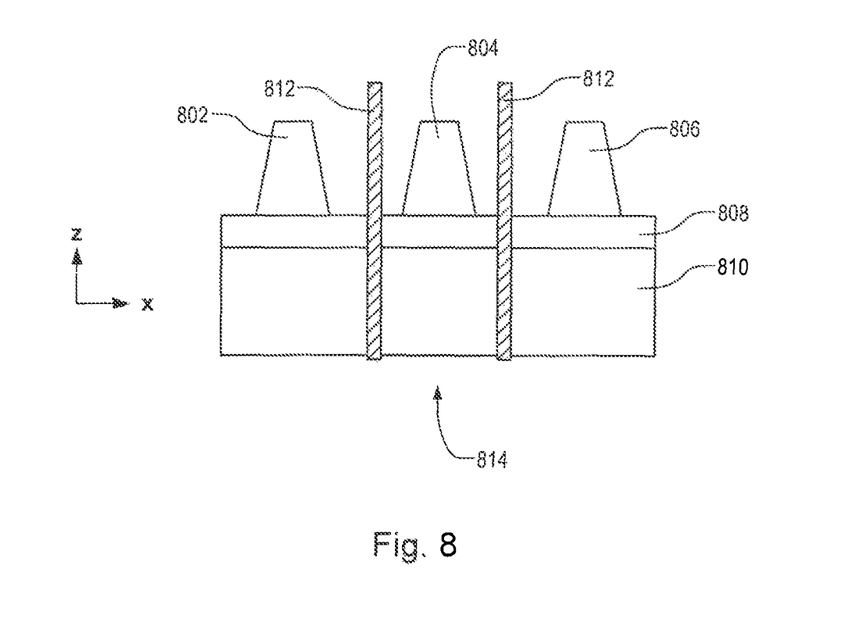
FIG. 8 illustrates single line computation using PMLs at the edges of the unit cell.

FIG. 8 illustrates single line computation with PMLs at the edges of the unit cell. Lines of the target grating 802, 804 and 806 are shown on a Bottom Anti-Reflective Coating (BARC) layer 808 and a silicon layer 810. A PML 812 is an artificial, ideally, absorbing layer that exponentially attenuates the outgoing waves radiated from the object 804. Like this, the object 804 is effectively decoupled from its neighbors 802 and 806 and the solution for a single line is found in the region 814 between the PMLs 812. This application of PMLs in RCWA was first described by Lalanne (Perfectly matched layers as a nonlinear coordinate transforms: a generalized formalization, Jean Paul Hugonin and Philippe Lalanne, JOSA A vol. 22, no. 9, September 2005) for the case of normal incidence only. For this case, the incident wave would not be affected by the PML.

Pisarenco, Maubach, Setija and Mattheij (Aperiodic Fourier modal method in contrast-field formulation for simulation of scattering of finite structures, Maxim Pisarenco, Jos Maubach, Irwan Setija and Robert Mattheij, JOSA A, vol. 27, nr. 11, November 2010) have extended the application of PMLs to arbitrary angles of incidence by using a scattered field formalism. With this aperiodic Fourier Modal Method in Contrast Field Formulation (aFMM-CFF), it has become possible to apply the principles of RCWA to compute diffraction from finite structures and small gratings. This allows rigorous modeling of finite structures using almost the same tools as periodic RCWA. However, there is still a sizable computational cost since the complete grating must be solved instead of only one period as in the periodic case. In standard RCWA, the object is discretized by a Fourier series in the periodic (x-) direction and spatially discretized in slices in the (z-)direction. The computational cost scales with $M \cdot N^3$ where M is the number of slices and N is the number of harmonics. This immediately shows the problem to extend this to finite gratings with hundreds of periods: the required number of harmonics scales proportional to the grating size and dramatically increases the computation time.

Figure 9:
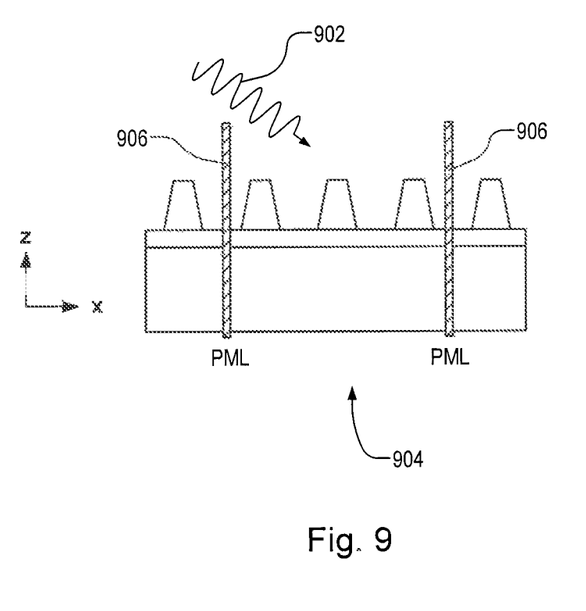
FIG. 9 illustrates modeling diffraction from a finite grating through periodization and placement of PMLs.

FIG. 9 illustrates modeling diffraction from a finite grating through periodization and placement of PMLs. Incident radiation 902 is scattered from the grating 904 in between the PMLs 906. It is clear that rigorous computation of diffraction from a small grating of 10×10 µm2 with a period of 100 nm takes a substantial computational effort. Resolving this periodicity with a 10 µm unit cell requires at least 100 harmonics. Modeling the finite size only in one dimension will lead to a numerical complexity of $O(M \cdot N^3)$ where M is the number of slices in the grating. Compare this to the complexity of an average periodic resist line at 5 harmonics (and the same number of slices), and the increase in computational cost will be painfully evident: $10^6 : 5^3 = 8 \cdot 10^3$.

Modeling the finite size in two dimensions squares the complexity with respect to harmonics $O(M \cdot N^6)$ which makes these problems impossible to compute on standard modern day computers.

Figure 1:
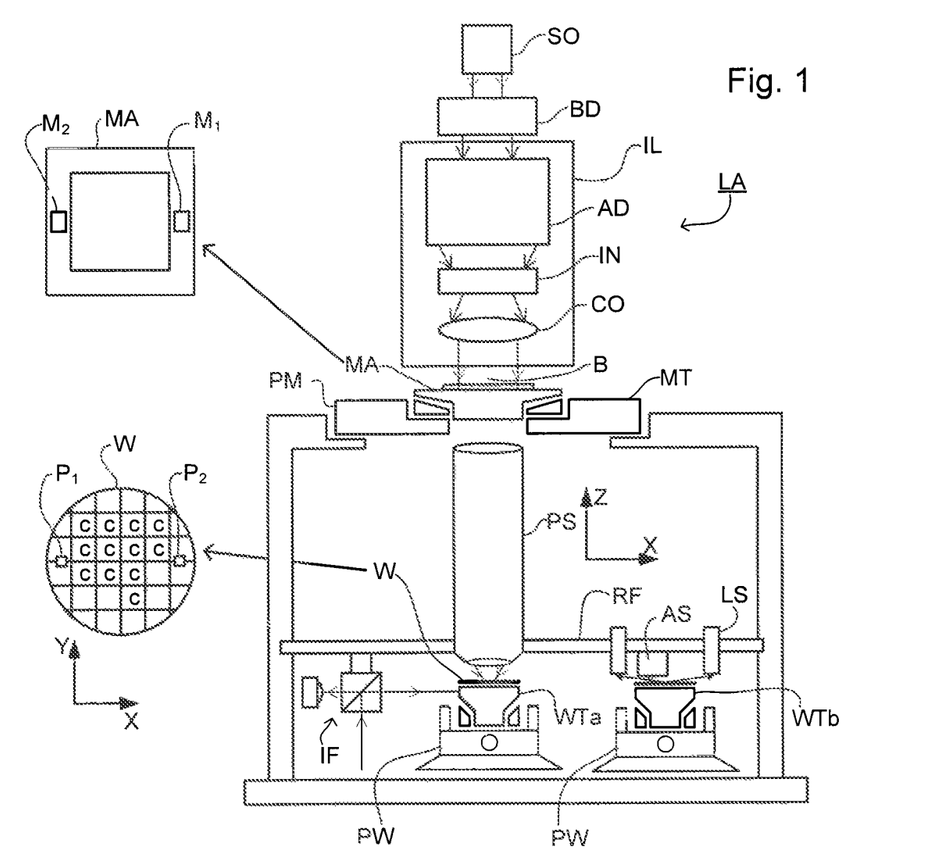
FIG. 1 depicts a lithographic apparatus.

FIG. 1 schematically depicts a lithographic apparatus. The apparatus comprises an illumination system (illuminator) IL configured to condition a radiation beam B (e.g. UV radiation or DUV radiation), a support structure (e.g. a mask table) MT constructed to support a patterning device (e.g. a mask) MA and connected to a first positioner PM configured to accurately position the patterning device in accordance with certain parameters, a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C comprising one or more dies) of the substrate W.

The illumination system may include various types of optical components, such as refractive, reflective, magnetic, electromagnetic, electrostatic or other types of optical components; or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position; for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate.

An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
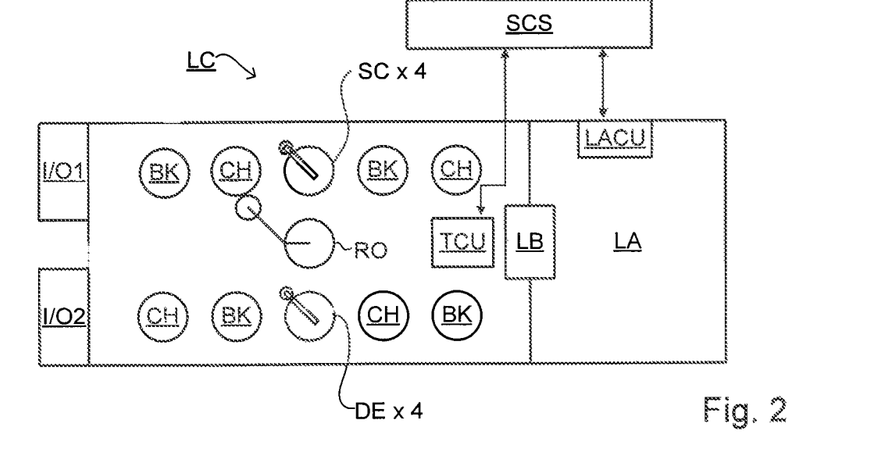
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot. RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
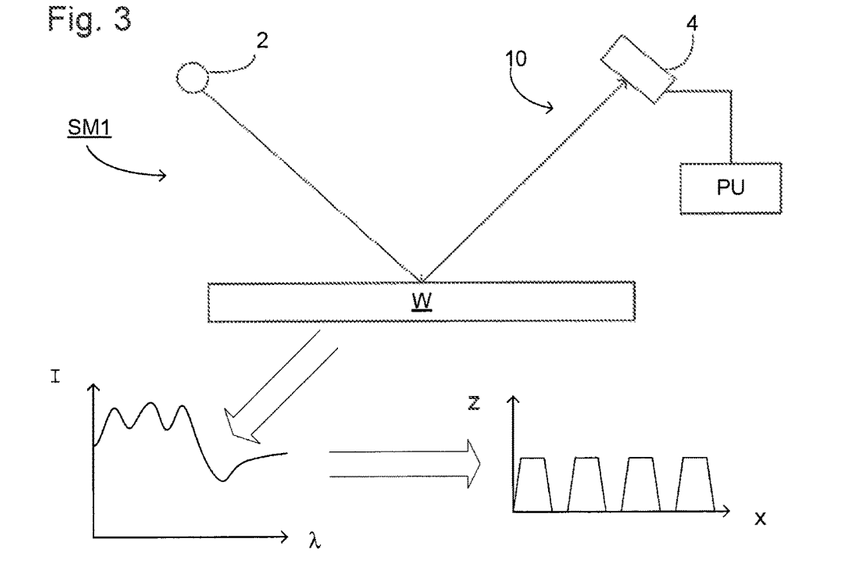
FIG. 3 depicts a first spectroscopic scatterometer.

FIG. 3 depicts a known scatterometer. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
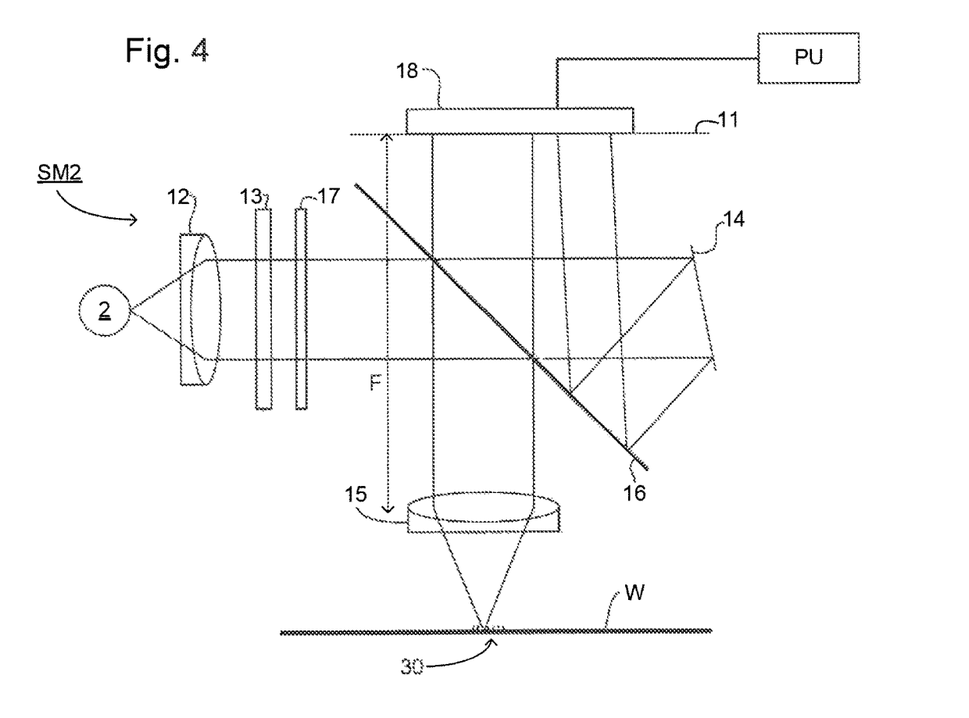
FIG. 4 depicts a second angular resolved scatterometer.

Another scatterometer that may be used with an embodiment of the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown)

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the target can be performed in a number of ways. In a first type of process, represented by FIG. 5, a diffraction pattern based on a first estimate of the target structure (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
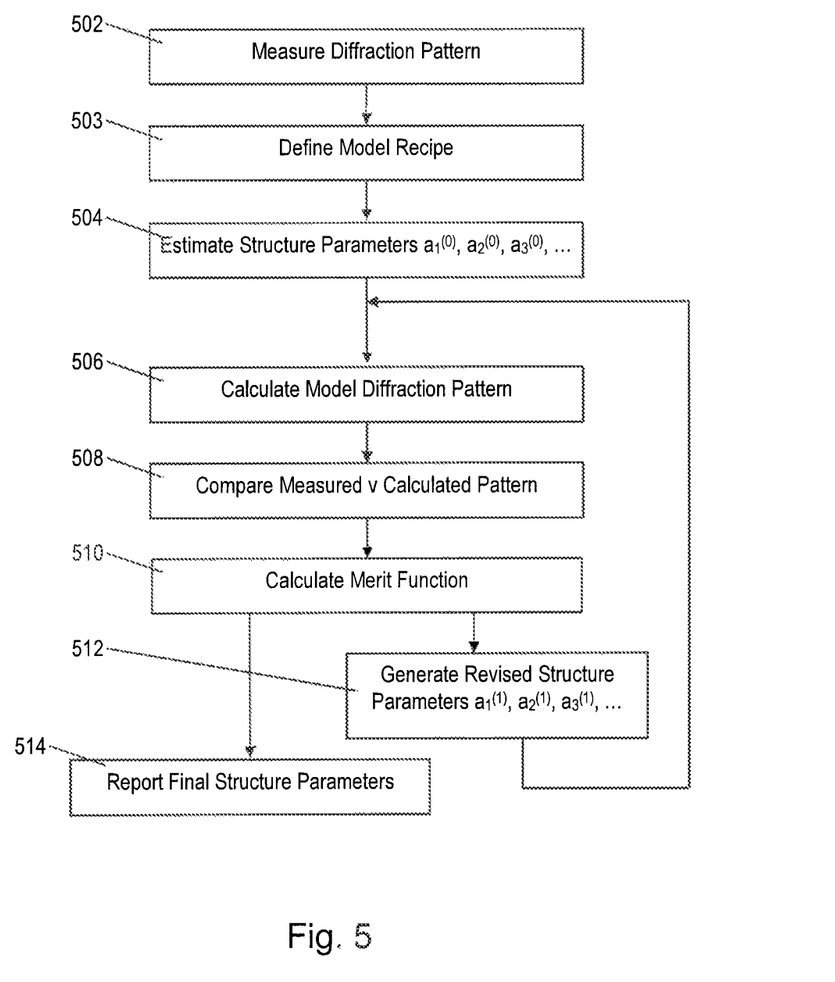
FIG. 5 depicts a first example process for reconstruction of a structure from scatterometer measurements.

Referring to FIG. 5 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters $a_i$ ($a_1$, $a_2$, $a_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 5, only the variable parameters are considered as parameters $p_i$.

In step 504: A model target structure is estimated by setting initial values $a_i^{(0)}$ for the floating parameters (i.e. $a_1^{(0)}$, $a_2^{(0)}$, $a_3^{(0)}$ and so on). Each floating parameter will be generated within certain predetermined ranges, as defined in the recipe.

In step 506: The parameters representing the estimated target structure, including shape together with the optical properties of the different elements of the model, are used to calculate the scattering properties, for example using a rigorous optical diffraction method such as RCWA or any other solver of Maxwell equations. This gives an estimated or model diffraction pattern of the estimated target structure.

In steps 508, 510: The measured diffraction pattern and the model diffraction pattern are then compared and their similarities and differences are used to calculate a "merit function" for the model target structure.

In step 512: Assuming that the merit function indicates that the model needs to be improved before it represents accurately the actual target structure, new parameters $a_1^{(1)}$, $a_2^{(1)}$, $a_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514: When the merit function indicates that this iterative process has converged on a solution with a desired accuracy, the currently estimated parameters are reported as the measurement of the actual target structure.

The computation time of this iterative process is largely determined by the forward diffraction model used, i.e. the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 502. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
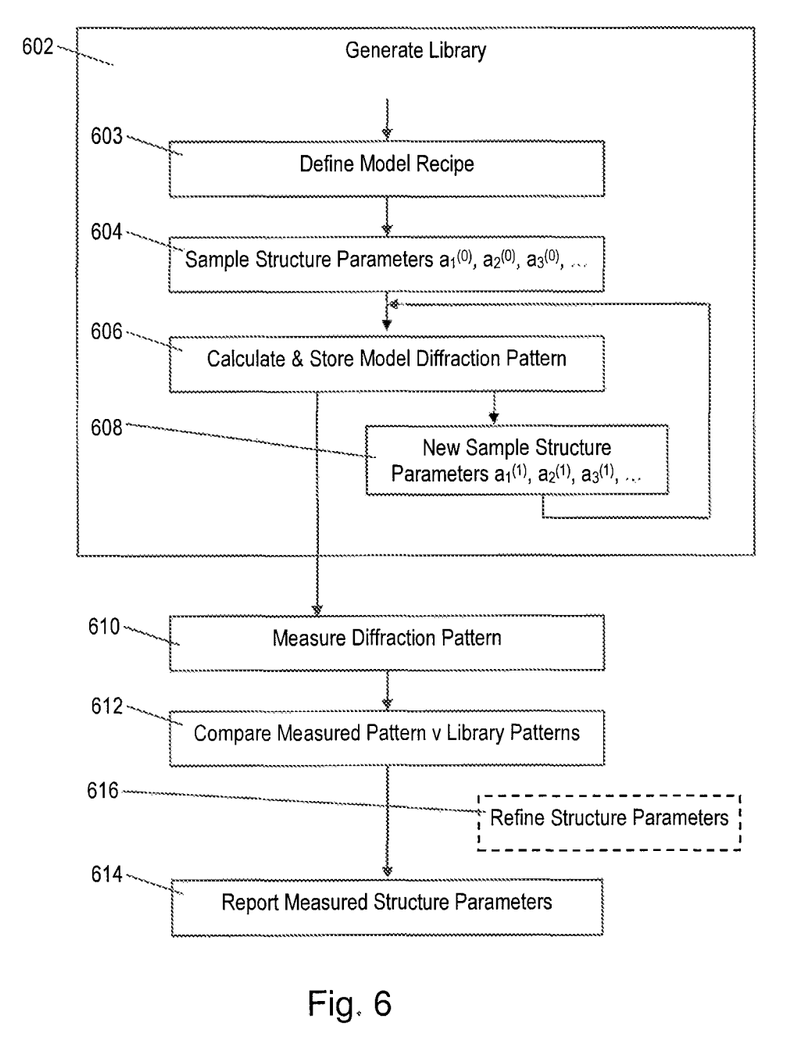
FIG. 6 depicts a second example process for reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

In step 602: The process of generating the library begins. A separate library may be generated for each type of target structure. The library may be generated by a user of the measurement apparatus according to need, or may be pre-generated by a supplier of the apparatus.

In step 603: A 'model recipe' is established which defines a parameterized model of the target structure in terms of a number of parameters a; ($a_1$, $a_2$, $a_3$ and so on Considerations are similar to those in step 503 of the iterative process.

In step 604: A first set of parameters $a_1^{(0)}$, $a_2^{(0)}$, $a_3^{(0)}$, etc. is generated, for example by generating random values of all the parameters, each within its expected range of val ties.

In step 606: A model diffraction pattern is calculated and stored in a library, representing the diffraction pattern expected from a target structure represented by the parameters.

In step 608: A new set of structure parameters $a_1^{(1)}$, $a_2^{(1)}$, $a_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610: After the library is generated (though it could be before), the real target 30 is placed in the scatterometer and its diffraction pattern is measured.

In step 612: The measured pattern is compared with the modeled patterns stored in the library to find the best matching pattern. The comparison may be made with every sample in the library, or a more systematic searching strategy may be employed, to reduce computational burden.

In step 614: If a match is found then the estimated target structure used to generate the matching library pattern can be determined to be the approximate object structure. The structure parameters corresponding to the matching sample are output as the measured structure parameters. The matching process may be performed directly on the model diffraction signals, or it may be performed on substitute models which are optimized for fast evaluation.

In step 616: Optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library, might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library, using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e. the calculation of the estimated model diffraction pattern using a rigorous optical diffraction theory from the estimated target structure.

Embodiments of the present invention provide a method to use the aFMM (RCWA on finite structures) very efficiently making the time to solve rigorous diffraction from a 10 μm grating at 100 nm pitch almost as fast as for one period of an infinite 100 nm grating. This performance may be achieved by changing the directions of spatial and spectral discretization and efficient re-use of scattering matrices.

In embodiments of the present invention, a structure periodic in the x-direction is discretized in the z-direction by a Fourier series and in the x-direction by slices. This increases the number of slices for spatial discretization $M_x$ to a few hundred, but keeps the number of Fourier harmonics $N_z$ low. This reduces the computational cost to something linear in the grating size. A further reduction of computation time is achieved by exploiting the repeating structure of a grating. After having described the scattering properties for one period, one does not need to solve it for the other periods. These so-called scattering matrices must, however, still be appropriately combined. Instead of sequentially coupling all the scattering matrices (which would still lead to a cost linear in the number of periods) the associative property of the Redheffer product (Difference equations and functional equations in transmission-line theory, in Modern Mathematics for the Engineer (1961), pp. 282-337. by R. Redheffer, edited by E. F. Beckenbach) for scattering matrices is exploited when combining scattering matrices. In this way the total scattering matrix from, for example, 2, 4, 8 . . . $2^k$ periods can be computed in a time that scales with $k=^2$log (number of periods).

Figure 10A:
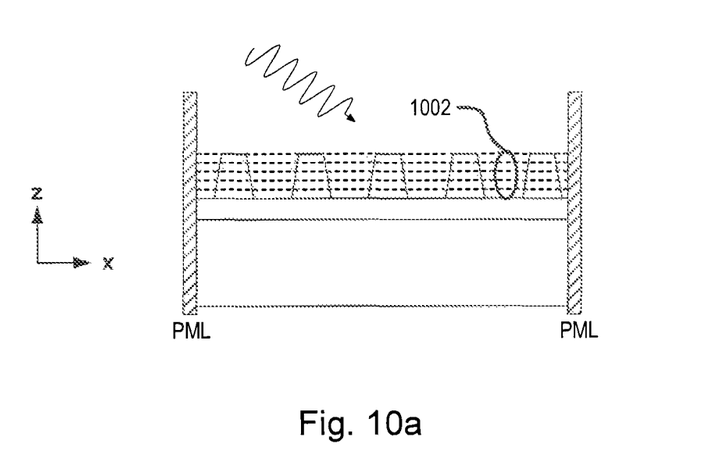
FIGS. 10a and 10b illustrate interchanging directions of spectral and spatial discretizations, with FIG. 10a illustrating the 0° case with M slices in z and FIG. 10b illustrating the 90° case with 2M slices per period in x.
Figure 10B:
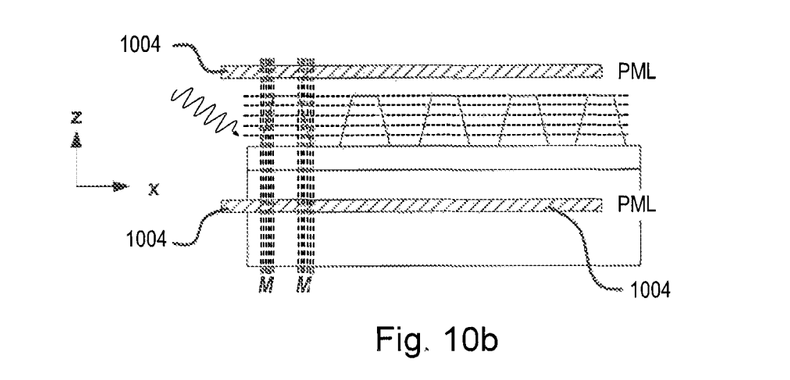

FIGS. 10*a* and 10*b* illustrate the exchange of directions of spectral and spatial discretizations.

With reference to FIG. 10*a*, in the known aFMM-CFF scheme, the spectral discretization takes place in the direction of finite periodicity (x-direction). In the z-direction, the object is sliced such that the profile of the grating lines is staircase-approximated. FIG. 10*a* illustrates the 0° case with $M_z$ slices in z 1002 (here $M_z$=5). In each slice the electric fields are expressed as a truncated sum over harmonic waves. By matching the electric and magnetic fields at the interfaces of each slice, the unknown coefficients of these harmonic waves in each slice can be solved for, leaving a system of equations for the reflection and transmission coefficients of the grating.

FIG. 10*b* illustrates an arrangement in accordance with an embodiment of the present invention, with a 90° rotation of the discretization direction compared to that illustrated in FIG. 10*a*. There are $2M_x$ slices per period in x. The PMLs 1004 are now placed as layers in the z-direction. The complexity of this numerical solution scales with $O(M_x \cdot N_z^3)$, where $M_x$ is the number of slices. The spatial discretization $M_x$ comes in linearly. For a cost estimation we can take the typical example of a resist grating on top of a BARC layer on silicon: taking 5 slices for the grating and the already mentioned 100 harmonics. A cost estimation for the case illustrated in FIG. 10*a* with x-spectral ($f_x$) and z-spatial (z) discretization may be represented by:

$$T(N_x, M_z) = (T_{eig} + T_{ETMA}) = \frac{1}{2} c M_z N_x^3 + \frac{1}{2} c M_z N_x^3 \sim 5 \cdot 10^6 \quad \text{(Equation 1)}$$

This notation requires some explanation: for every slice the Helmholtz equation must be solved which in Fourier space boils down to solving an eigenvalue problem. This complexity scales with $N_x^3$. Furthermore, the interface conditions between slices are recursively matched through the Enhanced Transmittance Matrix Approach (ETMA) which requires some matrix-matrix multiplications and inversions. These also scale with $N_x^3$. The computational effort for both operations ($T_{eig}$ and $T_{ETMA}$ respectively) will not be exactly the same, but in this cost estimation we shall make the approximation that they are; c is the proportionality constant linking the number of floating point operations to time. This assumption is motivated by practical simulations.

If we now rotate the discretization directions in accordance with an embodiment of the present invention, the spectral discretization takes place along the z-direction and the spatial discretization along the x-direction. This has a computational advantage for a finite periodic structure since the spectral discretization now only needs to resolve the structure over its height (generally a few 100 nm) requiring fewer harmonics and the spatial discretization repeats from line to line resulting in a linear dependence on grating size. For the example structure shown in FIG. 10*b*, we take 5 harmonics to model the z-dependence for the resist-on-BARC structure ($N_z$=5). The number of layers in the x-direction is now equal to the number of different slices which is equal to the number of periods $n_p$ multiplied by the number of slices per period. From FIG. 10*b*, we can see that discretizing the trapezoidal structure with the same resolution as in the 0° case illustrated in FIG. 10*a* requires $2M_x$ slices per period, of which only for $M_x$ slices the eigenvalue problem needs to be solved (the eigenvalue problem is the same for both sidewalls), The cost estimation for the case illustrated in FIG. 10b with x-spatial and z-spectral discretization may then be represented by:

$$T(M_x, N_z) = \tfrac{1}{2} M_x T_{eig} + n_p \tfrac{1}{2} 2 M_x T_{ETMA} = (\tfrac{1}{2} c M_x N_z^3 + n_p c \cdot M_x N_z^3) \sim 500 \cdot 5_3 = 6.25 \cdot 10^4 \quad \text{(Equation 2)}$$

The rotation of the x- and z-axes thus results in a speed-up factor of almost 100.

Note that this approach can only be applied to finite structures: it is only here that the radiative boundary conditions to $z=\pm\infty(x)$ can be substituted by a PML and the PML at $x=\pm\tfrac{1}{2}p$ can be replaced by radiative boundary conditions to $x=\pm\infty c$.

For repeating structures, like finite gratings, the computation can be improved even more by exploiting symmetry as the periods of the finite grating are all repeated. In the previous example illustrated in FIG. 10b the field was computed by propagating the field from slice to slice in the x-direction. The associative properties of the field propagation matrix per slice may be exploited in the so-called S-matrix formulation. With this associative property, from the single period S-matrix, the S-matrix for 2 periods can be constructed. From this 2-period S-matrix, the 4-period S-matrix, then 8-period S-matrix, and so on can be computed. Like this, the computational costs are even more reduced to give a cost estimation for x-spatial and z-spectral discretization with S-matrix doubling that may be represented by:

$$T_{eff}(M_x, N_z) = \tfrac{1}{2} M_x T_{eig} + \tfrac{1}{2}(2 M_x + \log(n_p)) T_{Smet} = (\tfrac{3}{2} c M_x N_z^3 + \tfrac{1}{2} c \log(n_p) N_z^3) \sim 10 \cdot 5^3 = 1.25 \cdot 10^3 \quad \text{(Equation 3)}$$

where we have separated the cost estimation in: 1) the computation of the eigenvalues for $M_x$ slices; 2) the recursive matching of interface conditions for $2M_x$ slices; and 3) computing the S-matrix for the double period.

With this improvement, the computational cost of computing rigorous diffraction from a 10 μm grating at 100 nm pitch may be reduced to almost the same cost as for the conventional RCWA computation for an infinitely periodic grating ($\sim 5 \cdot 5^3$). This is faster than any other known finite grating solver. Previous work in metrology research has compared the computational performance of standard RCWA to state-of-the-art commercial Maxwell solvers based on finite element techniques, Even there RCWA outperformed FEM with periodic boundary conditions. Since the computational cost for FEM scales roughly with the $4^{th}$ power of the object size in one dimension (because of spatial discretization), the aFMM-CFF outperforms FEM even more for finite gratings.

Figure 11:
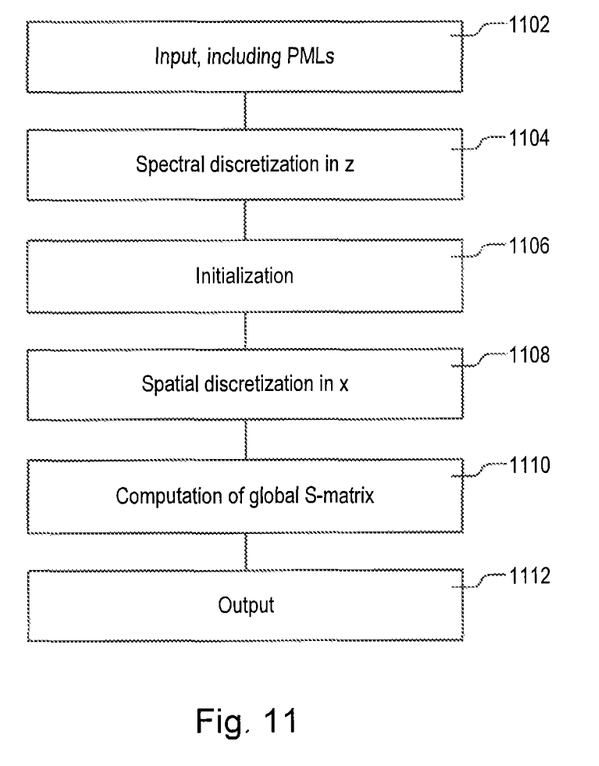
FIG. 11 is a flowchart of a method according to an embodiment of the present invention.

FIG. 11 is a flowchart of the RCWA method of calculating electromagnetic scattering properties of a structure in accordance with an embodiment of the present invention. The following steps are depicted.

In step 1102: Input: Specify geometrical setup, material distribution, and incident field, Model a pair of perfectly matched layers (PMLs) located spaced apart on either side of the grating in the direction of spectral discretization in a plane orthogonal to the direction of periodicity. Optionally, model perfectly matched layers (PMLs) located around an area of illumination of the finite periodic structure.

In step 1104: Spectral discretization orthogonal to the direction of periodicity in the direction of periodicity (z-direction, y-z plane). Optionally, set up normal-vector field for each layer, taking into account all the material boundaries and compute the Fourier transforms of this normal-vector field. Determine Fourier transforms of the permittivity and inverse permittivity for each layer.

In step 1106: Initialization: Set up Toeplitz matrices with Fourier coefficients (previous step) for each layer for the permittivity and inverse permittivity. Compute the inverse of the inverse permittivity matrices for each layer. Compose (multiply and add) the above matrices to form the total field-material interaction matrices for each layer. Set up matrices with wave vector components.

in step 1108: Spatial discretization in the direction of periodicity (x-direction, with slices in the y-z plane): Solve eigenvalue system for each layer.

In step 1110: Computation of global S-matrix: Set up linear systems that match the fields at the interfaces. Compute corresponding S-matrices for each interface combine S-matrices in a geometric progression using the Redheffer product In step 1112: Output: Compute reflection coefficients and/or diffraction efficiencies (diffraction patterns) from the obtained expansion coefficients.

The method described with reference to FIG. 11 may be used for calculating model diffraction patterns to reconstruct an approximate structure of the finite periodic structure from detected diffraction patterns, in accordance with the methods described with reference to FIGS. 5 and 6.

Finite size does not need to refer to finite gratings only. It can also refer to finite illumination spots on infinite gratings (the underfill situation used in known angularly resolved scatterometers). As is disclosed below, solving the diffraction problem in accordance with an embodiment of the present invention for a finite, coherent spot allows the total angular-resolved diffraction spectrum at the cost of just one 3-dimensional aFMM run.

Also here the periodic boundary conditions are not fullfilled by the incident field. As explained above, this is solved for known angularly resolved scatterometers by computing the angular resolved reflection spectrum from the incoherent addition of reflected plane waves from an infinitely periodic grating, Only in this way, the periodic boundary conditions can be fullfilled for each plane wave separately, but at the cost of computing a full forward solution at each incident angle (i.e. each detector pixel in the pupil plane of the scatterometer). In an embodiment of the present invention the reflection spectrum can be directly computed from a finite coherent illumination spot by placing the PMLs around the illuminated area of the grating.

Figure 12:
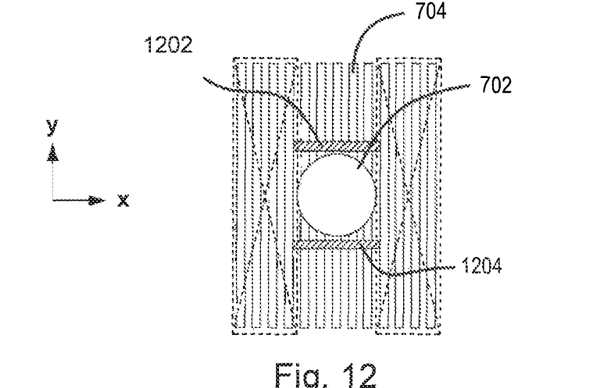
FIG. 12 illustrates modeling the underfill situation using PMLs

FIG. 12 illustrates modeling the underfill situation using PMLs. Note that in a typical angularly resolved scatterometer, illumination is incoherent, but for all dense gratings ($0^{th}$-order only) there is no difference between the angular resolved reflection spectrum from coherent and incoherent illumination since there is no interference between waves originating from different angles of incidence. For isolated gratings with regions of overlap between $0^{th}$- and $1^{st}$-orders, the incoherency must then be incorporated by incoherently adding the angular resolved spectra originating from different source points. How many of these source points are needed to properly model the incoherency is currently unknown.

If we focus on the coherent case, we can estimate the cost for computing the angular resolved spectrum using PMLs and compare that to the standard way.

To properly model a finite illumination spot, PMLs are placed above and below the grating and in the direction along the grating lines as shown in FIGS. 12 (1202 and 1204 respectively). This can be done by modeling finiteness along the direction of the lines and the extension of RCWA to model finite 3D objects. Alternatively, one can also employ the RCWA extension to 1D finite objects and decompose the illumination in the infinite y-direction in Fourier modes.

$$I(x,y)=I_0\int \Im(x,k_y)e^{-ik_y}dk_y \qquad \text{(Equation 4)}$$

By sampling the $k_y$-space we can construct a finite illumination spot from an infinite sum of functions that are finite in x and infinitely periodic in y. In practice we truncate this summation after a finite number of $k_y$ modes. In the pupil plane, this sampling of $k_y$ corresponds to sampling the sources of incident light discretely along the y-direction. In the x-direction, the local beam profile is used directly as input to the aFMM-CFF.

Figure 13A:
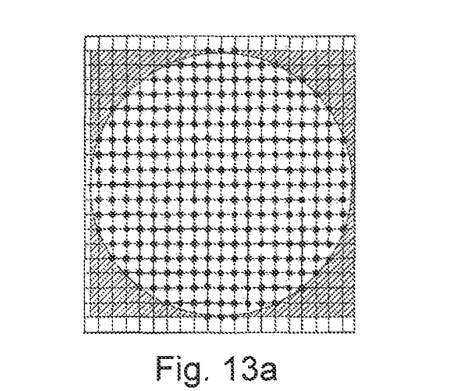
FIG. 13a illustrates full pupil plane sampling and FIG. 13b illustrates sampling the pupil plane in $k_y$.
Figure 13B:
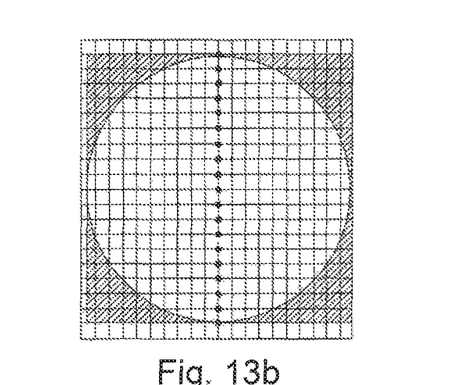

FIG. 13a illustrates full pupil plane sampling and FIG. 13b illustrates sampling the pupil plane in $k_y$.

Embodiments of the present invention provide a faster rigorous diffraction solver for non-periodic repeating structures, like gratings. They enable realtime CD reconstruction on finite gratings, as is now performed for infinitely periodic structures, but with a correct modeling of edge diffraction effects at almost the same computational cost.

Embodiments of the present invention also allow the computation of an angular-resolved spectrum from an angularly resolved scatterometer target (underfill situation) at one run of the rigorous diffraction model. This has the advantage that extra spectrum sampling points can be added to the reconstruction at no extra computational cost.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein. The computer program may be executed on a processor, such as processing unit PU in the scatterometer, The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:
1. A method comprising:
 illuminating, using an illumination system, a finite periodic structure with radiation, wherein the finite periodic structure comprises a direction of periodicity and was formed using a lithographic process of a lithographic apparatus;
 detecting, using a detection system, an electromagnetic scattering property arising from the illumination of the finite periodic structure using the illumination system;
 estimating, using a processing unit operatively coupled to the detection system, at least one structural parameter;

determining, using the processing unit, at least one model electromagnetic scattering property from the at least one structural parameter;

comparing, using the processing unit, the detected electromagnetic scattering property to the at least one model electromagnetic scattering property;

determining, using the processing unit, an approximate structure of the finite periodic structure based on the results of the comparison, wherein the model electromagnetic scattering property is calculated by numerically calculating electromagnetic scattering properties using spatial discretization of the finite periodic structure in the direction of periodicity and numerically calculating the electromagnetic scattering properties using spectral discretization of the finite periodic structure in a direction orthogonal to the direction of periodicity; and wherein the approximate structure of the finite periodic structure is configured to be used to make adjustments to the lithographic process for a subsequent substrate.

2. The method of claim 1, further comprising modeling a pair of matched layers spaced apart on either side of the finite periodic structure in the direction orthogonal to the direction of periodicity.

3. The method of claim 1, further comprising mod matched layers around an area of illumination of the finite periodic structure.

4. The method of claim 1, further comprising associatively combining scattering matrices of a plurality of periods of the finite periodic structure.

5. The method of claim 4, wherein the associatively combining scattering matrices comprises using a Redheffer product.

6. The method of claim 1, wherein the electromagnetic scattering properties comprise reflection coefficients.

7. The method of claim 1, wherein the electromagnetic scattering properties comprise diffraction patterns.

8. The method of claim 1, further comprising:
arranging a plurality of the model electromagnetic scattering properties in a library,
wherein the comparing comprises matching the detected electromagnetic scattering property to contents of the library.

9. An inspection apparatus comprising:
an illumination system configured to illuminate a finite periodic structure having a direction of periodicity with radiation, wherein the finite periodic structure was formed using a lithographic process of a lithographic apparatus;
a detector configured to detect an electromagnetic scattering property arising from the illumination of the finite periodic structure using the illumination system; and
a processor operatively coupled to the detection system and configured to:
estimate at least one structural parameter;
determine at least one model electromagnetic scattering property from the at least one structural parameter;
compare the detected electromagnetic scattering property to the at least one model electromagnetic scattering property; and
determine an approximate structure of the finite periodic structure from a difference between the detected electromagnetic scattering property and the at least one model electromagnetic scattering property,
wherein the processor is configured to determine the model electromagnetic scattering property by:
modeling a pair of matched layers spaced apart on either side of the finite periodic structure in a direction orthogonal to the direction of periodicity, and
numerically calculating electromagnetic scattering properties using spatial discretization of the finite periodic structure in the direction of periodicity and numerically calculating the electromagnetic scattering properties using spectral discretization of the finite periodic structure in the direction orthogonal to the direction of periodicity, and
wherein the approximate structure of the finite periodic structure is configured to be used to make adjustments to the lithographic process for a subsequent substrate.

10. The inspection apparatus of claim 9, wherein the processor is further configured to model other matched layers around an area of illumination of the finite periodic structure.

11. The inspection apparatus of claim 9, wherein the processor is further configured to associatively combine scattering matrices of a plurality of periods of the finite periodic structure.

12. The inspection apparatus of claim 11, wherein to associatively combine the scattering matrices the processor is further configured to use a Redheffer product.

13. The inspection apparatus of claim 9, wherein the electromagnetic scattering properties comprise reflection coefficients.

14. The inspection apparatus of claim 9, wherein the electromagnetic scattering properties comprise diffraction patterns.

15. The apparatus of claim 9, wherein the processor is further configured to:
arrange a plurality of the model electromagnetic scattering properties in a library; and
match the detected electromagnetic scattering property to contents of the library for the comparing.

16. The inspection apparatus of claim 9, wherein the finite periodic structure is located on a substrate that is exposed using the lithographic apparatus.

17. The inspection apparatus of claim 16, wherein the processor is further configured to:
determine an error in the exposure of the substrate; and
make adjustments to exposure of the subsequent substrate.

* * * * *

UNITED STATES PATENT AND TRADEMARK OFFICE
CERTIFICATE OF CORRECTION

PATENT NO. : 10,408,753 B2  
APPLICATION NO. : 13/490416  
DATED : September 10, 2019  
INVENTOR(S) : Pisarenco et al.

Page 1 of 1

It is certified that error appears in the above-identified patent and that said Letters Patent is hereby corrected as shown below:

In the Claims

In Claim 3, Column 19, Line 25, please delete "mod" and insert -- modeling --.

Signed and Sealed this  
First Day of December, 2020

Andrei Iancu  
*Director of the United States Patent and Trademark Office*